US012788974B2

(12) United States Patent
Töllner et al.

(10) Patent No.: US 12,788,974 B2
(45) Date of Patent: Nov. 10, 2026

(54) IMPLANTABLE LEAD ASSEMBLY

(71) Applicant: Berlin Heals GmbH, Berlin (DE)

(72) Inventors: Thomas Töllner, Ketzin (DE); Johannes Müller, Berlin (DE)

(73) Assignee: Berlin Heals GmbH, Berlin (DE)

( * ) Notice: Subject to any disclaimer, the term of this patent is extended or adjusted under 35 U.S.C. 154(b) by 0 days.

(21) Appl. No.: 19/043,048

(22) Filed: Jan. 31, 2025

(65) Prior Publication Data

US 2025/0295911 A1 Sep. 25, 2025

(30) Foreign Application Priority Data

Mar. 21, 2024 (EP) .................................... 24165369

(51) Int. Cl.
*A61N 1/20* (2006.01)
*A61N 1/05* (2006.01)

(52) U.S. Cl.
CPC ........... *A61N 1/205* (2013.01); *A61N 1/0565* (2013.01); *A61N 1/059* (2013.01)

(58) Field of Classification Search
CPC ....... A61N 1/205; A61N 1/0565; A61N 1/059
See application file for complete search history.

(56) References Cited

U.S. PATENT DOCUMENTS

| | | | | |
|---|---|---|---|---|
| 7,640,065 B1 | 12/2009 | Kroll | | |
| 2002/0055764 A1* | 5/2002 | Malonek | A61N 1/0587 | 607/122 |
| 2002/0103523 A1* | 8/2002 | Helland | A61N 1/056 | 607/122 |
| 2003/0023295 A1* | 1/2003 | Osypka | A61N 1/056 | 607/122 |
| 2005/0080471 A1 | 4/2005 | Chitre | | |
| 2019/0015659 A1* | 1/2019 | Müller | A61N 1/205 | |
| 2020/0114145 A1* | 4/2020 | Muller | A61N 1/0563 | |

FOREIGN PATENT DOCUMENTS

WO 2021198205 A1 10/2021

OTHER PUBLICATIONS

European Search Report for EP24165369.0, mailed Jun. 19, 2024 (8 pages).

Dragana Kosevic: "Cardio-microcurrent device for chronic heart failure: first-in-human clinical study", ESC Heart Failure, vol. 8, No. 2, Feb. 9, 2021 (Feb. 9, 2021), pp. 962-970, XP093165512, ISSN: 2055-5822, DOI: 10.1002/ehf2. 13242 * the whole document *.

* cited by examiner

*Primary Examiner* — Eugene T Wu

(74) *Attorney, Agent, or Firm* — Goodwin Procter LLP

(57) ABSTRACT

The present invention relates to an implantable lead assembly comprising an implantable first lead, an implantable second lead, and a control unit, to which the first and the second leads are electrically connected through connector lines, wherein the control unit is configured to establish a potential difference between the first and second leads so that an electric current can flow between the two leads, the first lead is configured to be positioned in the right ventricle of the heart, and the second lead comprises a coil comprising a central lumen passing longitudinally therethrough and an uninsulated portion at the distal end thereof, wherein the uninsulated portion is configured to be positioned in the coronary sinus and in a left lateral vein in the left ventricular myocardium.

25 Claims, 3 Drawing Sheets

IMPLANTABLE LEAD ASSEMBLY

CROSS REFERENCE TO RELATED APPLICATIONS

This application is a continuation of EP Application No. EP 24165369.0, filed Mar. 21, 2024. The contents of which are incorporated by reference herewith.

TECHNICAL FIELD

The present invention relates to an implantable lead assembly comprising an implantable first lead, an implantable second lead, and a control unit, to which the first and the second leads are electrically connected through connector lines, wherein the control unit is configured to establish a potential difference between the first and second leads so that an electric current can flow between the two leads, the first lead is configured to be positioned in the right ventricle of the heart, and the second lead comprises a coil comprising a central lumen passing longitudinally therethrough and an uninsulated portion at the distal end thereof, wherein the uninsulated portion is configured to be positioned in the coronary sinus and in a left lateral vein in the left ventricular myocardium.

TECHNOLOGICAL BACKGROUND

It has been shown that the application of microcurrent together with an electric field directly to the heart leads to an improvement of cardiac function in patients with heart failure (Kosevic, Dragana et al. "Cardio-microcurrent device for chronic heart failure: first-in-human clinical study." *ESC heart failure vol.* 8,2 (2021): 962-970). For this purpose, the microcurrent was applied between an epicardial patch lead placed extrapericardially or intrapericardially over the free wall of the left ventricle and a coil lead placed in the right ventricle. Examples of such patch leads are disclosed for example in WO 2016/016438 or in WO 2006/10132.

Furthermore, it could be shown that on the level of cultured cardiomyocytes, the application of microcurrent modulates myofibroblasts for cardiac repair and regeneration (Somesh D B et al. "Microcurrent-Mediated Modulation of Myofibroblasts for Cardiac Repair and Regeneration". *International Journal of Molecular Sciences.* 2024, 25, 3268. doi.org/10.3390/ijms25063268).

For the placement of the patch lead on the heart, the thorax is surgically opened, which is an invasive procedure that carries a certain degree of risk and is therefore less readily accepted by patients. It also requires collaboration between cardiologists and cardiothoracic surgeons, which makes the procedure more laborious. In addition, because a patch lead has a large conductive surface area compared to, for example, a common coil lead, the battery charge is also drained faster as a higher amperage is required to achieve the necessary current density to effectively treat the target tissue.

Thus, there is a need for a lead assembly system that can be transplanted microinvasively and that is capable of ensuring prolonged and effective treatment of the heart.

SUMMARY OF THE INVENTION

In order to address the need as explained above, it is an object of the present invention to provide a lead assembly that is transvenously implantable and enables effective and prolonged treatment of the heart and makes the system fully percutaneous implantable.

The invention provides an implantable lead assembly comprising an implantable first lead, an implantable second lead, and a control unit, to which the first and the second leads are electrically connected through connector lines, wherein the control unit is configured to establish a potential difference between the first and second leads so that an electric current can flow between the two leads, the first lead is configured to be positioned in the right ventricle of the heart, and the second lead comprises a coil comprising a central lumen passing longitudinally therethrough and an uninsulated portion at the distal end thereof, wherein the uninsulated portion is configured to be positioned in the coronary sinus and in a left lateral vein in the left ventricular myocardium.

According to an embodiment of the invention, the coil is a multi filar coil comprising 2 wires, 3 wires, 4 wires, 5 wires, 6 wires, 7 wires, or 8 wires, preferably 4 wires.

According to another embodiment of the invention, the uninsulated portion comprises a cap and/or a welded and polished area at the distal tip end thereof, preferably wherein the cap and/or the distal tip comprise an atraumatic cylindrical shape.

According to yet another embodiment of the invention, the uninsulated portion has a diameter between about 0.70 mm and about 1.10 mm, between about 0.75 mm and about 1.05 mm, even between about 0.80 mm and about 1.00 mm, between about 0.85 mm and about 0.95 mm, or between about 0.87 mm and about 0.92 mm, preferably about 0.9 mm.

According to one embodiment of the invention, the uninsulated portion has a length of at least about 20 mm, at least about 30 mm, at least about 40 mm, at least about 50 mm, at least about 60 mm, at least about 70 mm, at least about 80 mm, at least about 90 mm, or at least about 100 mm, preferably of at least about 50 mm.

According to a further embodiment of the invention, the uninsulated portion has a conductive surface of at least about 60 $mm^2$, at least about 90 $mm^2$, at least about 120 $mm^2$, at least about 150 $mm^2$, at least about 180 $mm^2$, at least about 200 $mm^2$, at least about 230 $mm^2$, at least about 260 $mm^2$, or at least about 290 $mm^2$, preferably of at least about 150 $mm^2$.

According to an embodiment of the invention, the second lead comprises a first insulation enclosing the connector line thereof in a first insulated portion proximal to the uninsulated portion and configured to be positioned in the coronary sinus.

According to a particular embodiment of the invention, the first insulation comprises a thickness of between about 0.05 mm and about 0.26 mm, between about 0.07 mm and about 0.23 mm, between about 0.10 mm and about 0.20, or between about 0.13 mm and about 0.17 mm, preferably about 0.15 mm, and/or wherein the first insulated portion has a diameter of between about 1.21 times and about 1.45, between about 1.24 times and about 1.42, between about 1.27 times and about 1.39, or between about 1.13 times and about 1.36, preferably about 1.33 times the diameter of the uninsulated portion.

According to another embodiment of the invention, the second lead comprises a second insulation enclosing the connector line thereof in a second insulated portion proximal to the first insulated portion and configured to be positioned in the right ventricle and the superior vena cava.

According to yet another embodiment of the invention, the second insulation comprises a thickness of between about 0.15 mm and about 0.55 mm, between about 0.20 mm and about 0.50 mm, between about 0.25 mm and about 0.45, or between about 0.30 mm and about 0.40 mm, preferably about 0.30 mm, and/or wherein the second insulated portion has a diameter of between about 1.38 times and about 2.18, between about 1.48 times and about 2.08, between about 1.58 times and about 1.98, or between about 1.68 times and about 1.88, preferably about 1.78 times the diameter of the uninsulated portion.

According to one embodiment of the invention, the uninsulated portion comprises a plurality of coil segments configured to be operable independently.

According to one particular embodiment of the invention, the uninsulated portion comprises at least 2 coil segments, at least 3 coil segments, at least 4 coil segments, at least 5 coil segments, at least 6 coil segments, at least 7 coil segments, or at least 8 coil segments, preferably 6 coil segments; and at most 12 coil segments, at most 11 coil segments, at most 10 coil segments, and at most 9 coil segments.

According to a further embodiment of the invention, the length of the coil segments is between about 3 mm and about 45 mm, between about 5 mm and about 40 mm, between about 6 mm and about 35 mm, between about 7 mm and about 30 mm, between about 8 mm and about 27 mm, between about 9 mm and about 23 mm, or between about 10 mm and about 20 mm; and/or wherein the length of the coil segments is between about 0.05 times and about 0.90 times, between about 0.10 times and about 0.80 times, between about 0.12 times and about 0.7 times, between about 0.14 times and about 0.60 times, between about 0.16 times and about 0.50 times, between about 0.18 times and about 0.4 times, or between about 0.20 times and about 0.30 times the length of the uninsulated portion.

According to an embodiment of the invention, the second lead comprises an attachment means at the distal end thereof, preferably wherein the attachment means has an anchor, hook, screw, or crutch shape; particularly preferably wherein the attachment means has an anchor or hook shape with an integrated blood seal.

According to one embodiment of the invention, the implantable lead assembly is configured for applying a microcurrent between the two electrodes for treating heart failure.

BRIEF DESCRIPTION OF THE DRAWINGS

The present disclosure will be more readily appreciated by reference to the following detailed description when being considered in connection with the accompanying drawings.

DETAILED DESCRIPTION OF PREFERRED EMBODIMENTS

Figure 1:
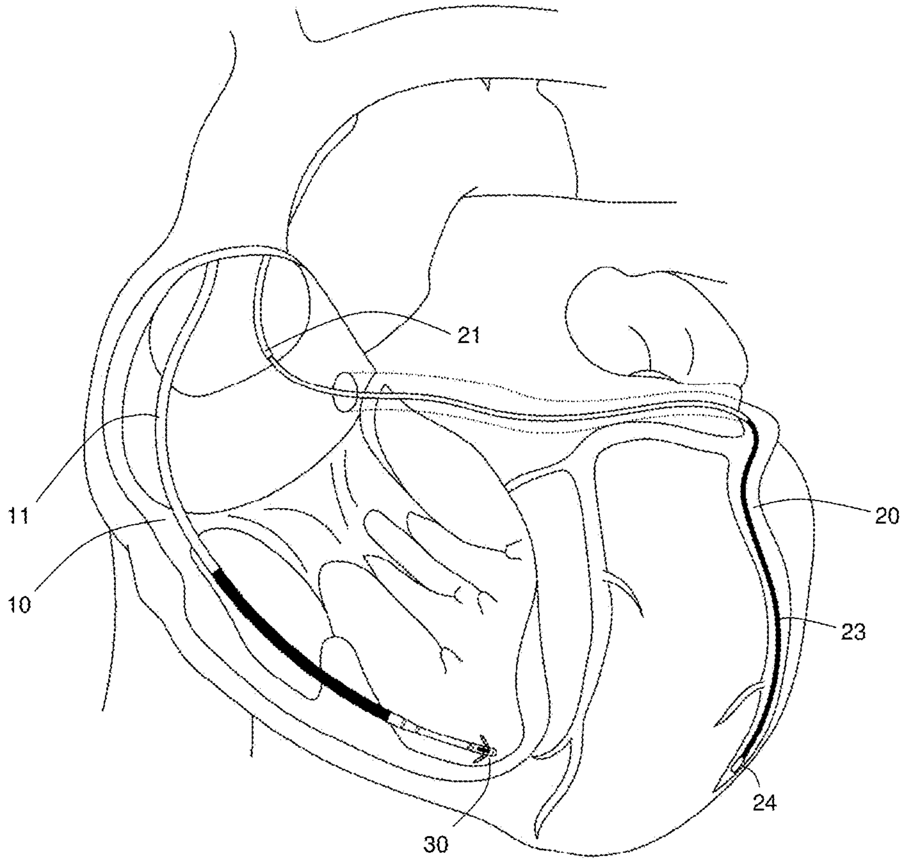
FIG. 1 is an illustration schematically showing the disposition of a lead assembly according to a preferred embodiment of the invention comprising a control unit (not shown) and first and second leads 10, 20, wherein the control unit is connected to the first and second leads 10, 20 via connector lines 11, 21, the first lead 10 is disposed inside the right ventricle of a heart, and the second lead 20 is disposed inside the left ventricular myocardium of the heart.
Figure 2:
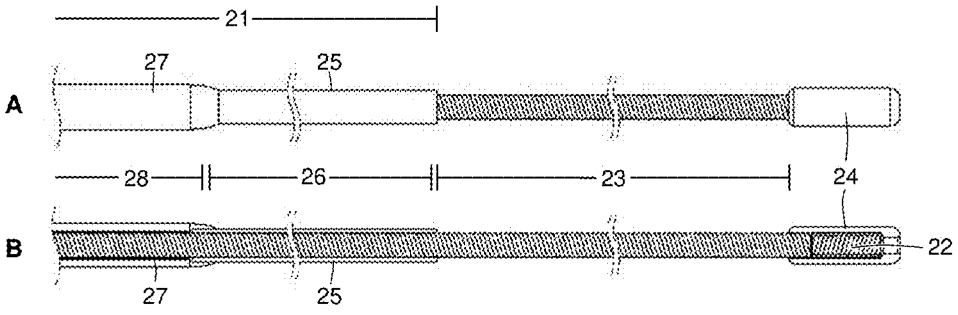
FIG. 2 is an illustration of a second lead 20 according to a preferred embodiment of the invention, schematically showing (A) a second lead 20 comprising a first insulated portion 26 and a second insulated portion 28, and (B) a sectional view of the second lead 20 according to the embodiment including a partial sectional view of the central lumen 22 at its distal tip.

In the following, the invention will be explained in more detail with reference to the accompanying figures. In the figures, like elements are denoted by identical reference numerals.

In order that the present description can be more readily understood, certain terms are first defined. Additional definitions are set forth throughout the detailed description.

It is to be noted that the term "a" or "an" entity refers to one or more of that entity; for example, "a coil segment," is understood to represent one or more coil segments. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, Korpas, David. *Implantable cardiac devices technology*. Berlin: Springer, 2013; Troutman, Leslie. "Dictionary of Medical Technology." RQ 32.3 (1993): 421-423, provide one skill in the art with a general dictionary of many of the terms used in this disclosure.

Units, prefixes, and symbols are denoted in their Système International d'Unités (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The terms “coil lead” or “wound lead” are used interchangeably herein and refer to a longitudinal implantable medical device. In this context, the terms “coil electrode” or “wound electrode” are used interchangeably herein and refer to the conductive portion of the lead capable of conducting electrical current through the organic tissue. It is to be understood that the design of the coil lead and electrode must ensure the main function thereof, i.e., the distribution of an electrical current through the organic tissue. Accordingly, in general, a coil lead is a component comprising at least one wire or thread wound in a coil shape. Such a coil lead usually comprises flexible biocompatible and biostable materials to fit the geometry of the target tissue.

The terms “mounted”, “attached”, “fixed”, and “fastened” are used to describe positioning or attaching of the lead to the organic tissue. In the context of the disclosure, the lead may be attached by being hooked to or screwed into organic tissue.

In the context of the invention, the term “organic tissue” refers to external or internal organs such as, for example, the brain, nervous tissue, heart, kidney, liver, stomach, intestine, gallbladder, pancreas, and skin.

The terms “biocompatibility” or “biocompatible” describe the appropriate biological requirements of a biomaterial or biomaterials used in a medical device as well as the ability of a material to perform with an appropriate host response in a specific application. In the context of the invention, the term “biocompatibility” specifically means the ability of the material of the assembly to function in vivo without eliciting detrimental local or systemic responses in the body. The term “biostability” or “biostable” refers to the ability of a material to maintain its physical and chemical integrity after implantation into a living tissue.

The term “current” refers to electric current and may be direct current or alternating current. During the intended medical treatment, the current density at the coil electrode will be adjusted to preferably 0.1 to 100 $\mu A/cm^2$, more preferably to 0.5 to 10 $\mu A/cm^2$.

Accordingly, the present invention provides an implantable lead assembly, preferably an implantable direct-current lead assembly, comprising an implantable first lead 10, an implantable second lead 20, and a control unit, to which the first and the second leads 10, 20 are electrically connected through connector lines 11, 21, wherein the control unit is configured to establish a potential difference between the first and second leads 10, 20, so that an electric current, preferably a direct current, can flow between the two leads 10, 20, the first lead 10 is configured to be positioned in the right ventricle of the heart, and the second lead 20 comprises a coil comprising a central lumen 22 passing longitudinally therethrough and an uninsulated portion 23 at the distal end thereof, wherein the uninsulated portion 23 is configured to be positioned in a left lateral vein in the left ventricular myocardium. The control unit also comprises a battery in which the electrical energy required to operate the lead assembly is stored.

According to a preferred embodiment of the invention, the implantable lead assembly is configured for applying a microcurrent between the two leads 10, 20 to the heart, preferably for treating heart failure.

The implantable lead assembly can be implanted transvenously, thus significantly reducing the invasiveness of the microcurrent method compared to the use of patch leads, resulting in less patient distress, and favoring clinical acceptance and frequency of use of the method.

The two flexible connector lines 11, 21 of the leads 10, 20, which are configured to run side by side from the control unit to the right atrium of the heart and branch there, and the control unit are electrically insulated against the environment. The control unit is configured to create a potential difference between the two distal electrodes of both leads 10, 20. The potential difference allows a electric current, preferably a direct current, to flow between the two distal electrodes.

The first lead 10 (hereinafter also referred to as right ventricular coil lead 10) comprises a coil electrode with an uninsulated portion 23 at its distal end that is configured to be positioned in the right ventricle. The length of the uninsulated portion 23 at the distal end of the first lead 10 is predetermined by the size of the right ventricular cavity between the tricuspid valve and the apical tip of the heart and may be between 6 and 8 cm. The right ventricular coil lead 10 may comprise an anchoring tip to be positioned preferably within the right ventricle touching the ventricular wall from the inside. However, any attachment means 30 known in the art may also be possible.

The second lead 20 (hereinafter also referred to as left ventricular coil lead 20) also comprises a coil electrode and has a smaller diameter than the right ventricular coil lead 10 since it has to enter the coronary sinus and is to be pushed into the tributary left lateral vein in the left ventricular myocardium, for example in the vena posterior ventriculi sinistri, alternatively or optionally into a descending coronary vein, primarily the marginal vein, the middle cardiac vein or the left posterior cardiac vein, preferably in the posterior cardiac vein, in the left heart muscle.

The coil of the left ventricular coil lead 20 is a hollow component with a central lumen 22 passing longitudinally therethrough and comprises an uninsulated (or exposed) portion 23 at its distal end.

In a preferred embodiment, at least one of the electrically conducting components outside of the control unit comprises a metallic material having properties of inherent corrosive resistance, high biocompatibility and/or radiopacity. These properties may be assessed by standards according to the ISO 10993 series, for example ISO 10993-15, ISO 10993-17 and/or ISO 10993-18 or the like. Conductive components outside the control unit may comprise the coil leads 10, 20 as well as the connector lines 11 and 21, but are not limited therein. Specifically, at least one of the connector lines 11, 21 or coil leads 10, 20 may comprise, be mainly composed of or are made of a conductive material with one or multiple of the above specified properties.

In a preferred embodiment, the coil electrodes of the left ventricular coil lead 20 and/or right ventricular coil lead 10 comprise a metallic material, wherein the metallic material is a metal alloy. The metal alloy may comprise platinum or is a platinum alloy such as a platinum-iridium alloy which has a low tendency to corrode due to its high positive standard potential (≥1.18 V). Platinum and its alloys have inherent corrosive resistance, high biocompatibility, and radiopaque properties, making it a suitable candidate for a range of medical applications.

In another preferred embodiment, all electrically conducting components outside of the housing, preferably made of or comprising titanium, of the control unit in the electrical conducive path are made of the same metallic material, wherein the metallic material exhibits properties of inherent corrosive resistance, high biocompatibility, and/or radiopacity. The use of the same metal material or the same group of alloys increases the stability against corrosion effects by avoiding electrochemical potential differences. Preferably, the metallic material is a metal alloy, such as a metal alloy comprising Platinum. Even more preferably, the metal alloy is an alloy composed of Platinum-Iridium.

At least one of the coil leads 10 or 20 together with their respective connector lines 11 and 21 may further be designed as a single structural element. In other words, the coil lead 10 and/or 20 with connector lines 11 and/or 21 may be configured as one piece. Accordingly, the inner conductor and the active electrode surface of each lead and connector line are designed as one structural element/component. This may mechanically stabilize the respective electrode over its entire length from the lead connector to the tip of the lead, since there are no potentially weak connection parts that may cause failure. This may minimize the risk of breakages during implantation, medical treatment and intended explantation. In general, it minimizes the risk of breakages in the case of applying any kind of stress, in particular tensile stress.

When a potential difference is applied between the two leads 10, 20 by means of the control unit, a direct current is flowing through the heart muscle in the ventricular area. Depending on the preferred direction of the current flow, the electrode of any of the leads 10, 20 can be set as a cathode or anode.

The control unit is preferably programmable to predetermine a time interval within which the potential difference is maintained to obtain the direct-current flow, which can range from some minutes, over an interval of 30 minutes or an hour until a number of hours, days or months, wherein the first lead 10 acts as the anode to define the current flow. After a predefined time, the current direction can be inverted, wherein the first lead 10 becomes the cathode, and a similar time interval is provided after such a first time interval. This changes the direction of the flow of the current. This sequence of change of current flow inversion can be continued for prolonged periods of time, e.g. for up to several months or even years.

It may also be possible to change the current strength while inverting the current flow since the impedance between the two leads 10, 20 can be dependent on the direction of the current flow. The amount of the direct current flow is predetermined to be far below the stimulation threshold, especially chosen to have a current density of 0.1 $\mu A/cm^2$ to 1 $mA/cm^2$. The control unit can comprise a control to maintain the current density below a maximum threshold.

Inverting a current flow has to be executed quasi-stationary, i.e., decreasing the current density over several minutes to zero and raising it with the opposite leading sign to the predetermined new direct current density level to avoid any rhythm disturbances which can potentially lead to dys- or arrhythmia.

It may be understood that the application of a direct current according to the invention is fundamentally different to the application of non-stationary, alternating currents or current pulses. In particular, current pulses are widely used for pacemaking or defribillation purposes. Such current pulses have typical pulse width of 0.5 ms to 1 ms (but are not limited thereto). It is thus clear for the person skilled in the art that such pulses used in the prior art contain a wide range of high frequency components, which stands in stark contrast to the characteristics of the presently used direct current.

Pacemakers have the function of emitting electrical impulses to the heart which trigger contractions of the heart if the heart's own impulse generators (e.g. sinus node) are not functional for whatever reason. To ensure that these impulses are delivered at the right time via the implanted electrode, a pacemaker is configured to constantly measure the heart's ECG and check whether or not the heart is generating its own impulses that can trigger a contraction. At the moment when the heart's own impulses are not registered, the pacemaker emits an electrical impulse of sufficient strength to trigger a contraction.

Pacemaker electrodes therefore have two functions: (i)—sensing the cardiac (intrinsic) ECG, and (ii)—conditionally emitting an electrical impulse that triggers a contraction.

Sensing the ECG is an important function in pacemaker therapy. To prevent oversensing (when inappropriate electrical activity is recognized as appropriate intrinsic cardiac activity) or undersensing (a lack of perception [permanent or intermittent] of cardiac signals), the electronic input circuit responsible for sensing has a filter characteristic that is typically tailored to the real ECG and is impermeable to direct current. Similarly, the pulses emitted by a pacemaker have no direct current component.

Defibrillators on the other hand are devices designed to detect arrhythmias (e.g. ventricular tachycardia or ventricular fibrillation) that are so pronounced that the heart can no longer pump sufficiently. If these are detected, defibrillators are configured to emit a strong electrical impulse (shock) to restore the heart's rhythm.

As with pacemakers, the ECG of the heart is continuously monitored via the sensor electrodes in order to detect corresponding ECG changes. Since it should be avoided as far as possible that shocks are erroneously delivered or that a necessary shock is not delivered, the electronic input circuits for sensing are equipped with appropriate filters that do not allow any direct current to pass. The shock pulses can be configured differently, but also have no direct current component.

Accordingly, current pulses according to the prior art may not be confused with the stationary or quasi-stationary direct currents discussed herein. In fact, the application of a direct current according to the invention has particular advantages for heart treatment as discussed in Dragana Kosevic et al.: "Cardio-microcurrent device for chronic heart failure: first-in-human clinical study", ESC HEART FAILURE, vol. 8, no. 2, 9 Feb. 2021.

The effective treatment of the heart by application of continuous microcurrent and a corresponding electric field is largely due to the fact that a wide distribution of the current and the electric field is achieved in the confined area of the myocardium. In the art, this has been accomplished by attaching a current-conducting patch lead, typically with a conductive area of approximately 20 to 35 $cm^2$, to the pericardium that surrounds the affected heart muscle wall, which is mostly the left ventricle, but could also be the right ventricle. Generally, a coil electrode is placed in the right ventricle and serves as the counter electrode. In the configuration with a patch lead attached to the pericardium and a right ventricular coil lead, the right ventricular coil lead is permanently in motion due to continuous cardiac motion, but the patch lead remains nearly stationary because the pericardium moves minimally during cardiac contraction.

In the arrangement of the invention, however, in which the patch lead is replaced by the left ventricular coil lead 20 in the venous coronary system, a different current and field distribution arises. The heart's three-dimensional movement, rotation and contraction, leads to a corresponding spatial distribution of current and voltage due to the movement of both leads' electrodes relative to each other. Both the right ventricular coil lead 10 in the right ventricle and the left ventricular coil lead 20 in the venous coronary system move freely in space. The continuous motion of the heart results in a three-dimensional distribution of fields that, despite the smaller area of the left ventricular coil lead 20 in the venous coronary system compared to a typical patch lead, leads to effective and widespread current and voltage penetration of the heart muscle.

The central lumen 22 of the left ventricular coil lead 20 allows implantation with the help of a coronary guidewire (Over the Wire (OTW)). OTW technique is well known in the art and one of the methodological pillars of percutaneous coronary intervention (PCI) and allows easy and precise guiding of medical devices to a certain area of the body. OTW technique generally involves, in a first step, guiding an atraumatic guidewire with controllable distal and proximal ends to a specific area of the patient's body utilizing natural or artificial body orifices or blood vessels and/or the central circulatory system. In a second step, the proximal end of the guidewire outside the body is inserted into a central lumen 22 of the medical device—in the context of the disclosure the hollow left ventricular coil lead 20—and the medical device is pushed, guided along the guidewire, in the intended atraumatic position in the target vessel (delivery). The guidewire is subsequently removed. OTW technique has the advantage over other implantation techniques in that the guidewire, because of its controllable distal and proximal ends and its much smaller diameter than the medical device to be implanted, can be safe and easily implanted by skilled personnel. The resulting guidance by the guidewire then enables precise and easy implantation of the medical device.

For the left ventricular coil lead 20 to be placed safely in the branched venous system of the heart, it needs to have the necessary flexibility to follow the twists and turns of the vascular system, the necessary tensile and compressive strength to be inserted easily and safely, and must be configured to be atraumatic.

The flexibility and the tensile and compressive strength of such a coil is determined by many factors such as the material properties of the wire used, the geometry and design of the coil and the wire (e.g., shape, diameter, and pitch), the coil structure, and the manufacturing techniques.

One way to achieve a favorable balance between good flexibility and good tensile and compressive strength of such a coil is to utilize a multi filar design instead of single filar coils. Multi filar coils (also referred to as "multi start", "multi-threaded", or "multi wire" coils) have multiple wires (or "starts") wound around the central axis. This design increases the effective pitch of the coil, allowing it to bear higher axial loads compared to a single filar coil with the same wire diameter and material while allowing an appropriate degree of lateral mobility. Due to the increased pitch, a multi filar coil is able to translate more axial pressure while having the same cross-sectional area/profile. The higher pitch can help to prevent localized stress concentrations that might lead to premature fatigue or failure, making multi-lead coils more durable. Multi filar coils can also exhibit reduced clastic and remaining elongation when pulled during implantation and explantation or after prolonged tension due to their larger pitch, which makes them more resistant to deformation under load over time. As such, according to a preferred embodiment of the invention, the left ventricular coil lead 20 is a multi filar coil comprising 2 wires, 3 wires, 4 wires, 5 wires, 6 wires, 7 wires, or 8 wires preferably 4 wires. The right ventricular coil lead 10 may also be a multi-filar coil with the same or a different amount of wires as the left ventricular coil lead 20.

Due to its structure as a wound coil, a coil lead generally comprises free wire end(s) at its terminals. Since the left ventricular coil lead 20 and the right ventricular coil lead 10 are pushed through the vascular system, the leading tip (hereinafter also referred to as "distal tip") thereof must be therefore configured such that it does not injure the tissue during this insertion process. Exposed wire ends at the distal tip end would likely cause injury to the tissue during the insertion process and make insertion significantly more difficult. For preventing injury to the tissue, according to a preferred embodiment of the invention, the uninsulated portion 23 of the left ventricular coil lead 20 comprises a cap 24 and/or a welded polished section at the distal tip end thereof, preferably wherein the cap 24 and/or distal tip comprises an atraumatic cylindrical shape. The cap 24 is configured to cover the wire ends but still allow the passage of a guide wire through it. Preferably, the cap 24 is firmly attached to the distal end of the tip, e.g., by welding, gluing, crimping, or a combination of these. The wire ends may also be welded together at the distal tip and the welded portion subsequently polished so that a smooth and even surface of the distal tip is obtained. It is to be understood that cap 24 and weld can be combined and that any shape of cap 24 and weld is possible that is atraumatic and presents as little resistance as possible to the blood vessels during insertion.

The left ventricular coil lead 20 is configured to enter the coronary sinus and is to be pushed into the tributary left lateral vein in the left ventricular myocardium, for example in the vena posterior ventriculi sinistri, alternatively or optionally into a descending coronary vein, primarily the marginal vein, the middle cardiac vein or the left posterior cardiac vein, preferably in the posterior cardiac vein, in the left heart muscle.

This has the advantage that a current can be applied directly in the myocardium. The left ventricular coil lead 20 should thereby preferably have a smaller diameter than the coronary sinus so as not to excessively obstruct blood flow. According to Gilard, et al. ("Angiographic anatomy of the coronary sinus and its tributaries." *Pacing and clinical electrophysiology: PACE* vol. 21,11 Pt 2 (1998): 2280-4), the middle cardiac vein has a mean diameter of 2.62+/−1.26 mm, the great cardiac vein has a mean diameter of 3.55+/−1.24 mm, and the left posterior vein(s) have a mean diameter of 2.25+/−1.2 mm. Accordingly, according to a preferred embodiment of the invention, the uninsulated portion 23 of the left ventricular coil lead 20 has a diameter between about 0.70 mm and about 1.10 mm, between about 0.75 mm and about 1.05 mm, even between about 0.80 mm and about 1.00 mm, between about 0.85 mm and about 0.95 mm, or between about 0.87 mm and about 0.92 mm, preferably about 0.9 mm.

The microcurrent together with the electric field is preferably to be applied directly in the myocardium over as large a tissue area of the heart as possible to ensure effective treatment of the heart. This can be achieved by dimensioning the uninsulated portion 23 of the left ventricular coil lead 20 about as long as the target marginal vein so that a field can be established that spans a large area of tissue. In addition, the left ventricular coil lead 20 should be positioned so that the maximum amount of damaged myocardium is between the two leads 10, 20, the electric field and current cover as large a volume of myocardium as possible, and the field that builds up between the leads 10, 20 is as homogeneous as possible to achieve the most uniform (homogenous) distribution of field and current. Accordingly, according to a preferred embodiment of the invention, the uninsulated portion 23 of the left ventricular coil lead 20 has a length of at least about 20 mm, at least about 30 mm, at least about 40 mm, at least about 50 mm, at least about 60 mm, at least about 70 mm, at least about 80 mm, at least about 90 mm, or at least about 100 mm, preferably of at least about 50 mm.

To improve cardiac function in patients with heart failure by applying microcurrent together with an electric field directly to the heart, a current density of preferably between 1.5 and 10 $\mu A/cm^2$ must be achieved. The current density is directly proportional to the conductive area and the amperage, i.e., the smaller the conductive area and/or the greater the amperage, the greater the current density. The microcurrent generator has a finite battery charge which discharges more quickly with increasing amperage. By configuring the conductive area of the leads 10, 20 to be small, less amperage is required to achieve a greater current density, thus enabling a longer battery life. Accordingly, according to a preferred embodiment of the invention, the uninsulated portion 23 of the left ventricular coil lead 20 has a conductive surface of at least about 60 $mm^2$, at least about 90 $mm^2$, at least about 120 $mm^2$, at least about 150 $mm^2$, at least about 180 $mm^2$, at least about 200 $mm^2$, at least about 230 $mm^2$, at least about 260 $mm^2$, or at least about 290 $mm^2$, preferably of at least about 150 $mm^2$.

It is to be understood that prior to implantation, the skilled professional determines and selects a left ventricular coil lead 20 of suitable diameter and length for the patient and the target veins.

According to a further preferred embodiment of the invention, the left ventricular coil lead 20 comprises a first insulation 25 enclosing the connector line 21 thereof in a first insulated portion 26 proximal to the uninsulated portion 23 and configured to be positioned in the coronary sinus. According to a particular preferred embodiment of the invention, the first insulation 25 of the left ventricular coil lead 20 comprises a thickness of between about 0.05 mm and about 0.26 mm, between about 0.07 mm and about 0.23 mm, between about 0.10 mm and about 0.20, or between about 0.13 mm and about 0.17 mm, preferably about 0.15 mm. According to an alternative preferred embodiment of the invention, the first insulated portion 26 of the left ventricular coil lead 20 has a diameter of between about 1.20 times and about 1.45, between about 1.24 times and about 1.42, between about 1.27 times and about 1.39, or between about 1.13 times and about 1.36, preferably about 1.33 times the diameter of the uninsulated portion 23.

According to a preferred embodiment of the invention, the left ventricular coil lead 20 comprises a second insulation 27 enclosing the connector line 21 thereof in a second insulated portion 28 proximal to the first insulated portion 26 and configured to be positioned in the superior vena cava. According to a particular preferred embodiment of the invention, the second insulation 27 of the left ventricular coil electrode comprises a thickness of between about 0.15 mm and about 0.55 mm, between about 0.20 mm and about 0.50 mm, between about 0.25 mm and about 0.45, or between about 0.30 mm and about 0.40 mm, preferably about 0.30 mm. According to another preferred embodiment of the invention, the second insulated portion 28 of the left ventricular coil lead 20 has a diameter of between about 1.38 times and about 2.18, between about 1.48 times and about 2.08, between about 1.58 times and about 1.98, or between about 1.68 times and about 1.88, preferably about 1.78 times the diameter of the uninsulated portion 23.

As shown in FIG. 1, the connector lines 11, 21 of the left ventricular coil lead 20 and the right ventricular coil lead 10 are configured to run side by side from the control unit (not shown) to the right atrium of the heart, from where they branch individually into the right ventricle and the coronary sinus. Because of its close proximity to the right ventricular coil lead 10 and the continuous movement of the heart, the second insulation 27 of the left ventricular coil lead 20 must be of greater thickness than the first insulation 25 to prevent insulation failure due to possible lead-to-lead abrasion between the left ventricular coil lead 20 and the right ventricular coil lead 10. The smaller diameter of the second insulated portion 28 further ensures that blood flow in the coronary sinus, which is narrower than the superior vena cava, is restricted as little as possible.

The first and second insulation 25, 27 preferably comprises a flexible material having good biocompatibility, chemical resistance, formability, and stability, such as, for instance, different medical grade silicones.

Figure 3:
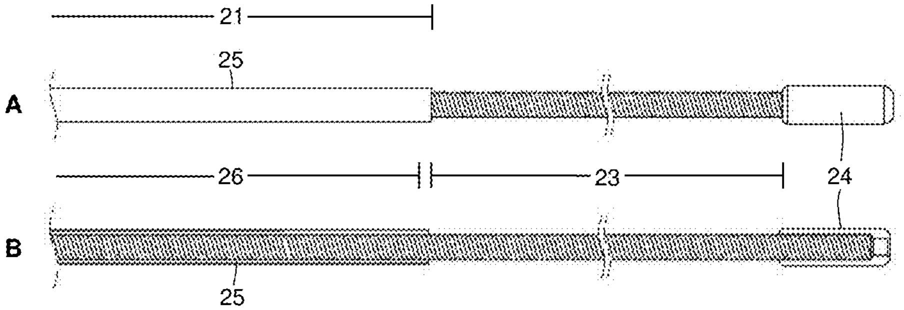
FIG. 3 is an illustration of a second lead 20 according to another preferred embodiment of the invention, schematically showing (A) a second lead 20 comprising only a first insulated portion 26, and (B) a sectional view of the second lead 20 according to the embodiment.

Referring to a preferred embodiment as shown in FIG. 3, the first insulation 25 enclosing the connector line 21 thereof in a first insulated portion 26 proximal to the uninsulated portion 23 is configured to have a substantially homogeneous thickness along the entire length of the insulated portion 26 of the connector line 21. In other words, the first insulation 25 is the only insulation used for the second lead 20, such that only one insulation is used for the entire length of the second lead 20. Accordingly, the first insulation 25 may be positioned in the coronary sinus as well as in the superior vena cava.

According to this particular preferred embodiment of the invention, the first insulation 25 of the left ventricular coil lead 20 comprises a thickness of between about 0.05 mm and about 0.26 mm, between about 0.07 mm and about 0.23 mm, between about 0.10 mm and about 0.20, or between about 0.13 mm and about 0.17 mm, preferably about 0.15 mm. According to an alternative preferred embodiment of the invention, the first insulated portion 26 of the left ventricular coil lead 20 has a diameter of between about 1.20 times and about 1.45, between about 1.24 times and about 1.42, between about 1.27 times and about 1.39, or between about 1.13 times and about 1.36, preferably about 1.33 times the diameter of the uninsulated portion 23.

Figure 4:
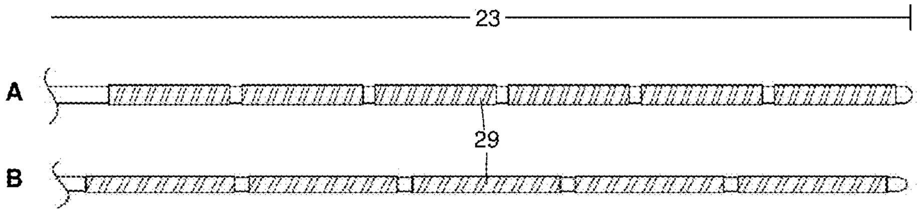
FIG. 4 is an illustration of a second lead 20 according to another preferred embodiment of the invention, schematically showing the uninsulated portion 23 of a second lead 20 (A) comprising 6 independent coil segments 29, and (B) comprising 5 independent coil segments 29.
Figure 5:
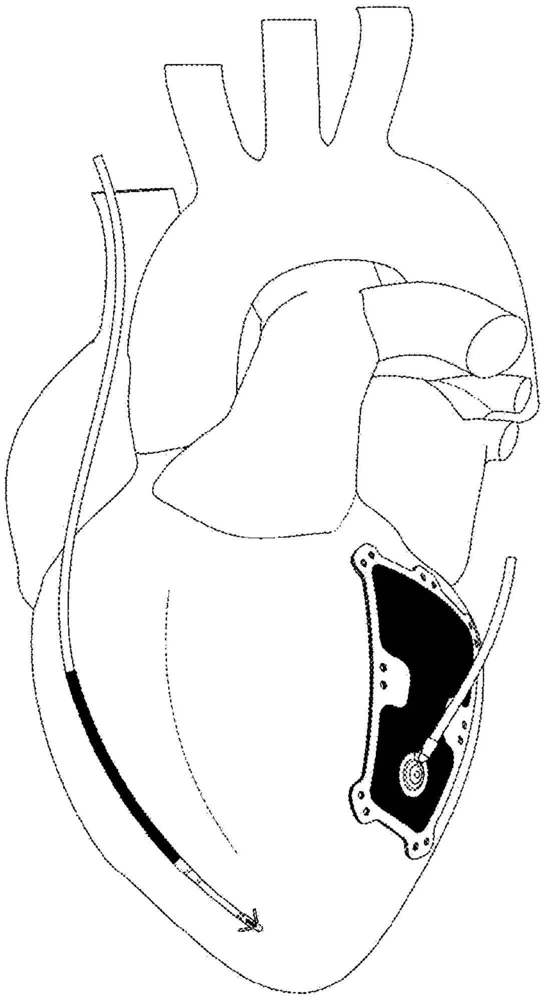
FIG. 5 is an illustration schematically showing the disposition of an internal coil electrode and an external flat electrode according to a comparative example in and outside of a heart.

In another specific embodiment of the invention, as shown in FIG. 4, the uninsulated portion 23 comprises a plurality of coil segments 29 configured to be operable independently. These coil segments 29 are configured to be activated or deactivated depending on their position and the desired therapy zone, providing greater flexibility in tailoring the therapy to the patient's individual needs. In cases where extensive therapy over a larger electrode surface is required, multiple segments can be activated. This enables broad treatment of the desired zone. In cases, however, where special caution is necessary to avoid undesirable effects such as, for instance, therapy current by-pass, where the therapy current is redirected through the bloodstream and the coronary sinus to the right ventricular coil lead 10, or phrenic nerve stimulation, only a single or a few coil segment(s) 29 may be activated. This enables for greater targeting and adaptability of the therapy to the individual circumstances of each patient. The coil segments 29 thus enable an improvement in treatment efficacy and a reduction in undesirable effects. Furthermore, a more homogeneous electrical field and current distribution can be obtained by the selection of distinct segments of the lead.

According to one particular preferred embodiment of the invention, the uninsulated portion 23 comprises at least 2 coil segments 29, at least 3 coil segments 29, at least 4 coil segments 29, at least 5 coil segments 29, at least 6 coil segments 29, at least 7 coil segments 29, or at least 8 coil segments 29, preferably 6 coil segments 29; and at most 12 coil segments 29, at most 11 coil segments 29, at most 10 coil segments 29, and at most 9 coil segments 29.

According to a further preferred embodiment of the invention, the length of the coil segment 29 is between about 3 mm and about 45 mm, between about 5 mm and about 40 mm, between about 6 mm and about 35 mm, between about 7 mm and about 30 mm, between about 8 mm and about 27 mm, between about 9 mm and about 23 mm, or between about 10 mm and about 20 mm. According to another preferred embodiment of the invention, the length of the coil segment 29 is between about 0.05 times and about 0.90 times, between about 0.10 times and about 0.80 times, between about 0.12 times and about 0.7 times, between about 0.14 times and about 0.60 times, between about 0.16 times and about 0.50 times, between about 0.18 times and about 0.4 times, or between about 0.20 times and about 0.30 times the length of the uninsulated portion 23.

In any of the embodiments herein, the first and/or second insulation 25, 27 may be mechanically fixed to the respective coil leads 10, 20 and/or connector lines 11, 21. Preferably, the mechanical fixation may be implemented by at least one stable bond positioned between the insulation of the first and/or second insulation 25, 27 and the inner conductor of coil leads 10, 20 and/or connector lines 11, 21. In a preferred implementation, stable bonds will be applied at each end of the first and/or second insulation 25, 27. This may further minimize the risk of deformation and breakages during implantation and intended explantation.

According to a preferred embodiment of the invention, the left ventricular coil lead 20 comprises an attachment means 30 at the distal end thereof, preferably wherein the attachment means 30 comprises an anchor, hook, screw, or crutch shape; particularly preferably wherein the attachment means 30 comprises an anchor or hook shape with an integrated blood seal.

The attachment means 30 is configured for securely anchoring the left ventricular coil electrode at the target tissue, enables stable positioning of the electrode and ensures efficient conductivity for the medical application. As shown in FIG. 1, attachment means 30 may also be used in the right ventricular coil lead 10.

The attachment means 30 may be selected from the list comprising anchors or barb hooks which may engage with the surrounding tissue, thereby ensuring a firm positioning of the lead, screws or threaded spirals located at the distal tip end of the lead and screwable into the tissue, mechanical fasteners including clips and clamps, and tissue Integration and capsule formation of connective tissue capsule around the lead over time which stabilizes the electrode and provides a natural anchor. It is to be understood that the suitable attachment means 30 is selected by the skilled person and depends on various factors, such as the application of the lead, tissue typology, and anticipated stresses. The inventive attachment means 30 is preferably configured to ensure secure, biocompatible, and durable anchoring.

All embodiments of the present invention as described herein are deemed to be combinable in any combination unless the skilled person considers such a combination to not make any technical sense.

The invention claimed is:

1. An implantable lead assembly comprising an implantable first lead, an implantable second lead, and a control unit, to which the implantable first lead and the implantable second lead are electrically connected through connector lines of the control unit, wherein:

the control unit is configured to establish a potential difference between the implantable first lead and the implantable second lead to allow a non-stimulating, continuous direct electric current flow between the implantable first lead and the implantable second lead;

the implantable first lead is configured to be positioned in a right ventricle of a heart; and the implantable second lead comprises a coil comprising a central lumen passing longitudinally therethrough and an uninsulated portion at a distal end thereof, wherein the uninsulated portion is configured to be positioned in a vein tributary to a coronary sinus.

2. The implantable lead assembly of claim 1, wherein the control unit is programmable to predetermine a time interval within which the potential difference is maintained to obtain the non-stimulating, continuous direct electric current flow and/or wherein the control unit comprises a control to maintain a current density below a stimulation threshold up to 1 $mA/cm^2$.

3. The implantable lead assembly of claim 1, wherein the uninsulated portion is configured to be positioned in the left lateral vein.

4. The implantable lead assembly of claim 1, wherein the coil is a multi filar coil comprising 2 to 8 wires.

5. The implantable lead assembly of claim 1, wherein the uninsulated portion comprises a cap and/or a welded polished section at a distal tip end thereof.

6. The implantable lead assembly of claim 1, wherein the uninsulated portion has a diameter between about 0.70 mm and about 1.10 mm.

7. The implantable lead assembly of claim 1, wherein the uninsulated portion has a length of at least about 20 mm.

8. The implantable lead assembly of claim 1, wherein the uninsulated portion has a conductive surface of at least about 60 $mm^2$.

9. The implantable lead assembly of claim 1, wherein at least one of the implantable first lead, the implantable second lead, and one or both of the connector lines comprise a metallic material.

10. The implantable lead assembly of claim 1, wherein the implantable first lead, the implantable second lead, and the connector lines are made of the same metallic material.

11. The implantable lead assembly of claim 1, wherein the implantable first lead with the corresponding connector line and/or the implantable second lead with the corresponding connector line comprise an electrically conductive material.

12. The implantable lead assembly of claim 1, wherein the implantable second lead comprises a first insulation enclosing the connector line thereof in a first insulated portion proximal to the uninsulated portion.

13. The implantable lead assembly of claim 12, wherein the first insulation is configured to have a substantially homogeneous thickness along an entire length of the first insulated portion.

14. The implantable lead assembly of claim 13, wherein the first insulation is configured to be positioned in the coronary sinus and a superior vena cava.

15. The implantable lead assembly of claim 12, wherein the first insulation comprises a thickness of between about 0.05 mm and about 0.26 mm and/or a diameter of between about 1.20 times and about 1.45 times a diameter of the uninsulated portion.

16. The implantable lead assembly of claim 12, wherein the implantable second lead comprises a second insulation enclosing the connector line thereof in a second insulated portion proximal to the first insulated portion.

17. The implantable lead assembly of claim 16, wherein the second insulation comprises a thickness of between about 0.15 mm and about 0.55 mm and/or a diameter of between about 1.38 times and about 2.18 times a diameter of the uninsulated portion.

18. The implantable lead assembly of claim 1, wherein the uninsulated portion comprises a plurality of coil segments configured to be independently operable.

19. The implantable lead assembly of claim 18, wherein a length of each coil segment is between about 3 mm and about 45 mm and/or between about 0.05 times and about 0.90 times a length of the uninsulated portion.

20. The implantable lead assembly of claim 1, wherein the implantable second lead comprises an attachment means at the distal end thereof, preferably wherein the attachment means comprises an anchor, hook, screw, crutch shape, or an integrated blood seal.

21. The implantable lead assembly of claim 1, wherein a current density of the non-stimulating, continuous direct electric current flow is 0.1 to 100 μA/cm$^2$.

22. A method for treatment or prevention of heart failure, comprising the steps of:

implanting a first lead, wherein the first lead is configured to be positioned in a right ventricle of a heart, implanting a second lead, wherein the second lead comprises a coil comprising an uninsulated portion at a distal end thereof, wherein the uninsulated portion is configured to be positioned in a vein tributary to a coronary sinus, and establishing a potential difference between the first lead and the second lead, so that a non-stimulating, continuous direct electric current flows between the two leads.

23. The method of claim 22, wherein the potential difference is maintained to obtain the non-stimulating, continuous direct electric current flow over a predetermined time interval and/or wherein a current density is maintained below a stimulation threshold up to 1 mA/cm$^2$.

24. The method of claim 22, wherein the uninsulated portion is configured to be positioned in the left lateral vein.

25. The method of claim 22, wherein the coil comprises a central lumen passing longitudinally therethrough.

* * * * *